United States Patent
Kulmala et al.

(10) Patent No.: US 9,377,433 B2
(45) Date of Patent: Jun. 28, 2016

(54) ACCURATE INTEGRATED LOW-COST ELECTRODE CHIPS FOR POINT-OF-NEED ANALYSIS AND A METHOD OF UTILIZATION IN HOT ELECTRON-INDUCED ELECTROCHEMILUMINESCENT SYSTEMS

(75) Inventors: Sakari Kulmala, Kirkkonummi (FI); Antti Niskanen, Espoo (FI); Samuli Franssila, Helsinki (FI); Tiina Ylinen-Hinkka, Espoo (FI)

(73) Assignee: LABMASTER OY, Turku (FI)

(*) Notice: Subject to any disclaimer, the term of this patent is extended or adjusted under 35 U.S.C. 154(b) by 441 days.

(21) Appl. No.: 13/703,418

(22) PCT Filed: Jun. 10, 2011

(86) PCT No.: PCT/FI2011/000031
§ 371 (c)(1),
(2), (4) Date: Feb. 1, 2013

(87) PCT Pub. No.: WO2011/154589
PCT Pub. Date: Dec. 15, 2011

(65) Prior Publication Data
US 2013/0206611 A1    Aug. 15, 2013

(30) Foreign Application Priority Data

Jun. 11, 2010   (FI) .................................... 20100246
Jun. 15, 2010   (FI) .................................... 20100251

(51) Int. Cl.
*G01N 21/66*   (2006.01)
*G01N 27/327*  (2006.01)

(52) U.S. Cl.
CPC ............ *G01N 27/3276* (2013.01); *G01N 21/66* (2013.01)

(58) Field of Classification Search
USPC ..................................................... 204/403.15
See application file for complete search history.

(56) References Cited

U.S. PATENT DOCUMENTS

| 6,251,690 B1 | 6/2001 | Kulmala |
| 7,005,108 B2 | 2/2006 | Ala-Kleme et al. |
| 2004/0189311 A1 | 9/2004 | Glezer et al. |
| 2009/0009756 A1* | 1/2009 | Yamamichi et al. .......... 356/246 |
| 2009/0178924 A1 | 7/2009 | Ala-Kleme et al. |

FOREIGN PATENT DOCUMENTS

| JP | 2009204375 A | 10/2009 |
| WO | WO2006103313 A1 * | 10/2006 |

OTHER PUBLICATIONS

PCT/FI2011/000031—International Search Report; Oct. 3, 2011 (4 pgs).

(Continued)

Primary Examiner — Jill Warden
Assistant Examiner — Julie Tavares
(74) Attorney, Agent, or Firm — Berggren Inc.

(57) ABSTRACT

The invention relates to integrated electronic chip (IEChip) cartridge devices which are used in hot electron-induced electrochemiluminescence methods and to instrumentation based on the electrical excitation of label molecules with subsequent measurement of luminescence in order to quantitate analyte concentrations especially in bioaffinity assays, especially outside of central laboratories.

7 Claims, 6 Drawing Sheets

(56) References Cited

OTHER PUBLICATIONS

Niskanen, A.J. et al; Ultrathin tunnel insulator films on silicon for electochemiluminescence studies; http://www.sciencedirect.com/science?_ob=ArticleListURL&_method=list&_ArticleListID=415461684&_sort=r&_st=13&view=c&_acct=C000228598&_version=1&_urlVersion=0&_userid=10&md5=14c217a3f08edef8c8e4346a671658c2&searchtype=a (abstract), Aug. 3, 2009.

Niskanen, A.J. et al; Integrated microelectrode hot electron electrochemiluminescent sensor for mircofluidic applications; http://www.sciencedirect.com/science/article/pii/S0925400510007689 (abstract), Feb. 20, 2011.

* cited by examiner

SEQUENCE LISTING

<160> NUMBER OF SEQ ID NOS: 2

<210> SEQ ID NO 1
<211> LENGTH: 26

```
<212> TYPE: DNA
<213> ORGANISM: artificial sequence
<220> FEATURE:
<223> OTHER INFORMATION: chemically synthesized

<400> SEQUENCE: 1
ttagccgcat tcaggggcg aaaaaa                                          26

<210> SEQ ID NO 2
<211> LENGTH: 21
<212> TYPE: DNA
<213> ORGANISM: artificial sequence
<220> FEATURE:
<223> OTHER INFORMATION: chemically synthesized

<400> SEQUENCE: 2
gaaacacgga cacccaaagt a                                              21
```

ACCURATE INTEGRATED LOW-COST ELECTRODE CHIPS FOR POINT-OF-NEED ANALYSIS AND A METHOD OF UTILIZATION IN HOT ELECTRON-INDUCED ELECTROCHEMILUMINESCENT SYSTEMS

PRIORITY

This application is a national entry of PCT/FI2011/0000031 filed on Jun. 10, 2011 which claims priority of FI20100246 filed on Jun. 11, 2010 and of FI20100251 filed on Jun. 15, 2010, all of which are fully incorporated herein by reference.

SEQUENCE LISTING

This application contains sequence data provided on a computer readable diskette and as a paper version. The paper version of the sequence data is identical to the data provided on the diskette.

FIELD OF INVENTION

The present invention relates to analytical methods and devices exploiting the phenomenon of electrochemiluminescence. The invention is especially suitable for need-of-point type of analysis, such as point-of-care analysis.

BACKGROUND OF INVENTION

Presently, there is a general burden need for fast, sensitive and quantitative diagnostic technologies. Such ones are suitable for wide market areas including public health, research, farming, environmental care, veterinary medicine, and certain industrial production areas. Improved sensitivity, speed, robustness, stability, and decreased cost per analysis are factors, which after being accomplished in diagnostic technologies, can find applications in quite new areas.

Very high sensitivity can be obtained with certain diagnostics instruments, but they are too expensive. On the other hand, certain methods can be enough inexpensive, exemplified by immunochromatography, but they are not applicable to certain needs of the market. Any technology, wherein a set of such demands are met, will have an important place in the future diagnostics and a huge market potential.

There is a number of different analytical principles in practical use in diagnostics: for example, assays based on radioactivity, enzyme-linked immunosorbent assay (ELISA), colorimetric assays, and assays based on fluorescence, and chemiluminescence including anodic as well as hot electron-induced (cathodic) electrochemiluminescence (ECL). The hot electron-induced ECL is described in detail in U.S. Pat. No. 6,251,690, Kulmala S., et al. Each of these techniques has their role as regards to the integral of sensitivity, robustness, stability, speed, and price. The differences between the techniques reflect the function of physical limitations or advantages of the methods. For example, a drawback of the application based on radioactive compound is the decay of the label within a period of time and the extra cost of radioactive waste from both the safety and environmental viewpoint. The application of the most sensitive assays on diagnostics is limited by the complicated nature of the tests and instruments, and only experts can perform the assays. The complexity of the assay is generally directly proportional to the price of the instrument and/or the test. In the context of complex instruments, it could be mentioned the anodic electrochemiluminescence techniques now becoming more and more popular: the instrument is a complicated laboratory robot, the handling of which needs expertise and where the measuring process involves repeated washes and preparative steps. They are factors that increase the cost of the analyses as well as increase the amount of waste and therefore will make this method impossible for the needs of small laboratories, doctors offices etc. (bedside or point of care analytics).

Commercially beneficial methods are based on the principle that the substances to be analyzed are identified and measured in mixtures by so-called label substances. In the measurements based on unique properties of biological molecules, as in immunochemical assays, the analyte to be measured (X) can be selectively sorbed from a mixture of molecules to solid-phase bound antibodies and then the bound molecules are measured with another labeled antibody selectively binding to (X). The label substances can be radioactive isotopes, enzymes, light absorbing, fluorescent or phosphorescent molecules, certain metal chelates etc., which are linked covalently to the antibody. Alternatively, the purified (X) can be marked and the amount of unknown unlabeled sample (X) can be measured by a competition reaction. The assays for DNA and RNA can be also based on the selective binding (bioaffinity). Also many other chemical and biochemical analyses can be carried out by the same principles. In order to decrease the cost and/or increase the measuring accuracy, there is presently a tendency to measure several different parameters at the same time in the sample. One possibility is to use lapels snowing fluorescence or phosphorescence at different wavelength or possessing different luminescence lifetimes. Different measuring principles and strategies, which can be used in immunodiagnostics, have been described in the book The Immunoassay Handbook, Edited by David Wild, Stockton Press Ltd., New York, 1994, on pages 1-618.

It is known in the prior art that organic substances and metal chelates are beneficial as label substances and that they can be excited by light or by electrochemically to produce luminescence specific to the label. These methods are particularly sensitive and are well suitable. However, because the measured concentrations are extremely low, there are also case-dependent difficulties; the use of fluorescence can be disturbed, among other things, by Tyndall, Rayleigh and Raman scattering. When measuring biological substances, there is, almost without exception, after the excitation pulse, a fast-discharging high background fluorescence. Phosphorescence in the solution phase can be utilized mostly only with chelates between lanthanide ions and specially synthesized organic molecules. The drawback of the excitation techniques with the photoluminescent labels is the complexity of the instruments and the high price of the sensitive optical components.

In general, the advantage of ECL is the low price of the electrical excitation components and simpler optics. Compared to the photoluminescence, several drawbacks can be avoided. Traditional anodic electrochemiluminescence with inert metal electrodes can be carried out with organic luminophores by a relative simple instrument in non-aqueous solvents. However, in bioaffinity assays, where the biggest commercial expectations are concentrated to, water solutions are applied. Biological samples are taken nearly always in non-organic solutions and therefore the measuring system should work in aqueous or at least in micellar water solutions. Only a very limited number of transition metal chelates are working as ECL-labels in anodic ECL in water or micellar solutions.

Thus far the commercially most important analytical chemical application of the anodic ECL is the method using derivatives of Ru(bpy)$_3^{2+}$-chelate, where the detection phase of the label occurs in micellar phase. As known from textbooks, the micellar mixtures are always prone to different disturbing effects due to the uncontrolled complexity of the micellar equilibria. The similar systems can be used also in very small detection cells in capillary electrophoresis systems (A. Aurora et al., Anal. Comm. 34 (1997) 303-395.).

The hot electron-induced ECL, which does not depend on micelles has many crucial advantages over the anodic ECL. It can be applied both to immuno- and DNA hybridization methods (see, Blackburn, G., et al., 1991, Clin. Chem. 37: 1534-1539; Kenten, J., et al. 1992, Clin. Chem. 33: 873-879). The immunoassays and DNA or RNA probe applications by Roche Diagnostics Ltd. exploit magnetic particles by which the label substance is brought onto golden working electrode (Massey; Richard J., et al. U.S. Pat. No. 5,746,974; Leland; Jonathan K., et al. U.S. Pat. No. 5,705,402). The reproducible handling of magnetic latex particles is however in many ways difficult, therefore this method is useful only in expensive laboratory robots (e.g. Elecsys 1010 and 2010) having a complicated and precise liquid handling system. In addition, the permanent massive golden work electrode needs long cleaning and pretreatment between each analysis (Elecsys Service Manual, p. 70).

Although in many respect superb, a drawback in the hot electron-induced ECL (HECL) in bioaffinity assays is the need of long incubation time in order to get the reacting molecules into equilibrium, which is necessary to optimize the analytical accuracy. Later, it was found out that a significant improvement in the performance could be acquired with placing a thin porous film on the work electrode, and by producing CIPF-devices (US2009178924 (A1), Ala-Kleme et al.).

In the conventional electrochemistry, electrodes are some times integrated on the same plane, but theoretically, this should not be working while using hot electron electrochemistry, since the HECL should be emitted only in the outer edges of working electrode (cathode) closest to the counter electrode. However, while testing we found out that, for some reasons in the electrolytic cell having sufficiently high volume of electrolyte solution the HECL is emitted evenly over the whole working electrode surface even if the counter electrodes are situated in the same plane on an electrode chip (integrated electrode chips, IEChip) normally made of insulating materials such as glass, ceramics or organic polymers.

Labmaster Ltd (Turku, Finland) has worked with their diagnostics strip for almost ten years and the solution developed by them is rather archaic device containing a single piece of oxide-coated silicon embedded in plastics and an essential multipurpose membrane to input samples and reagents for the bioaffinity assays (US2009178924, Ala-Kleme et al.). The major drawback of these strips is that all the measurements are carried out in an instrument's cell which has to be very carefully washed and cleaned between each measurement to avoid carry-over and the deterioration of the counter electrode built in the instrument is also problematic.

The present invention provides means to construct truly disposable cartridges with extremely accurate and reproducible electrodes and which naturally also provide highly accurate results in practical analysis. The present invention discloses highly sophisticated and accurate methods to construct IEChips from silicon and many insulating substrates. The present invention can be used in connection of Labmaster's CIPF devices to increase their quality (silicon-based IEChips) or keep the quality unchanged but decrease the production costs (glass and plastics-based IEChips). But, more importantly, many other types of the cartridge types can easily be designed not needing cumbersome membranes to speed up the bioaffinity reactions. Especially the ingenious solutions to construct IEChip variants from silicon are revolutionizing the accuracy and reproducibility of the point-of-need type of analysis utilizing HECL. Presently no other methods can offer such a rapid and accurate analysis results with extraordinary low detection limits in the point-of-need markets as the future cartridges using the present IEChip innovations.

According to the present invention, a significant improvement in the performance of CIPF-devices (US2009178924 (A1), Ala-Kleme et al.) and, in addition, totally new types of highly accurate disposable HECL cartridges containing IEChips can be obtained, as well as the novel analytical methods utilizing the cartridges as described in the claims 1-7.

DETAILED DESCRIPTION OF THE INVENTION

Figure 1:
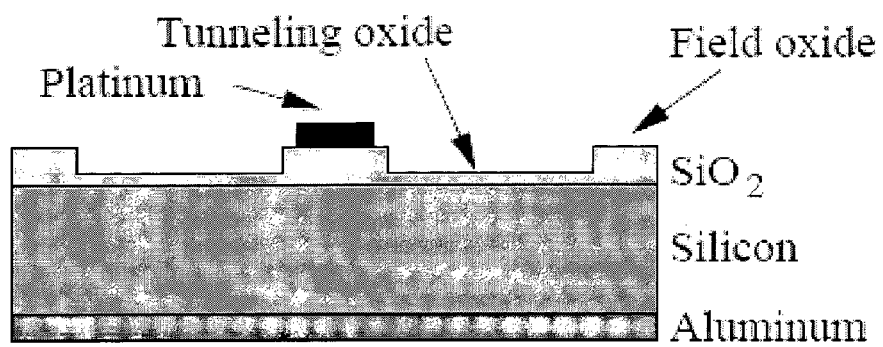
FIG. 1. Cross-sectional views of silicon (a) and glass (b) devices. Vertical and lateral dimensions are not to scale.
Figure 1:
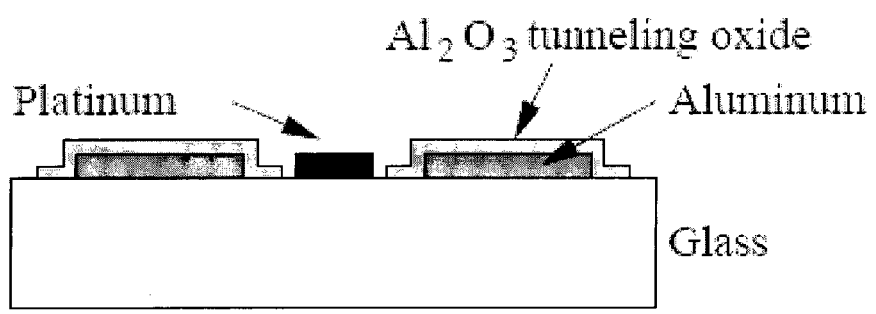

According to the present invention, different analyses can be performed with simple and inexpensive devices equally well as with more complicated devices, whenever the actual immunoassay or DNA hybridization is done with the porous film on the surface of IEChip (CIPF-IEChip device). Thus, a considerable improvement to earlier CIPF devices can be created, the measuring instrument and the measuring cartridge are sufficiently low-cost for the point-of-need analysis and can be manufactured to be fully disposable. Thus, no carry-over between analyses can be occurring and the manufacturing of CIPF-IEChip cartridges will become much easier when no separate working electrodes and counter electrodes must be introduced in the cartridge.

In addition, the electrode materials are low-cost when sufficiently large batch are produced and the production of both the IEChips alone and, finally, the CIPF-IEChip cartridges and other type of IEChip cartridges is very simple and relatively easy. The present invention discloses different variants of CIPF-IEChip device types and cartridges involving CIPF-IEChips and other types of IEChip cartridges.

In the current invention, the counter electrode has been e.g. fabricated onto the working electrode's surface on a silicon chip, and a sample cell chamber is formed on the chip by bonding a cast-molded polydimethylsiloxane (PDMS) lid to the electrode chip. This makes a fully integrated HECL sample cell which is convenient to use, and being fully disposable, also eliminates the risk of sample cross-contamination. Thus the device as such is usable in point-of-care analytical applications. In an optical detection device, PDMS is an ideal material due to its high optical transparency over the wide wavelength range of 240-1100 nm, as well as being electrically insulating and chemically inert towards aqueous reagents.

An alternative sample containment scheme, utilizing patterned hydrophobic films, is also disclosed. While PDMS fluidics is easily fabricated in volume using a master mold, the bonding of the PDMS cover to the HECL chip is an extra fabrication step, whether done on the chip or wafer scale. Hydrophobic surface modification, on the other hand, is a simple wafer-scale deposition step, and patterning is readily effected by a single photolithographic step and lift-off. Hydrofobic surface modification allows simple ways of carrying out bioaffinity assays also using porous membranes on the IEChips which makes the incubation periods very short and assay becomes very rapid.

The current HECL devices are fabricated using thermally oxidized silicon as the working electrode and platinum thin film counter electrodes, which attain sub-nanomolar sensitivity to the Tb(III) chelate used as the model analyte. A glass device with sputtered aluminum thin films coated with atomic layer deposited (ALD) alumina as the working electrode, is also disclosed to demonstrate the feasibility of deposited electrodes on insulating substrates.

This invention forms a significant improvement over the prior art to CIPF devices and methods intended onto point-of-need markets by making possible manufacturing of low-cost but highly accurate quantitative rapid tests and test cartridges. We have earlier noticed that the same principles can be utilized by manual fabrication with even cheaper materials, but the accuracy of such a devices is very far away of the devices disclosed in the present invention although the price of the final cartridges is not substantially higher when the present methodology is applied and sufficiently large volume of production has been achieved. It is believed that these types of HECL "Rolls Royce chips in the price of GM" and subsequent cartridges are strongly needed in the diagnostic markets in addition to the less accurate ones constructed by screen-printing or other printing techniques of lower quality materials which quite probably can not satisfy physicians high quality needs. Example 8 discloses wide variety of solutions for different type of cartridges for special uses. The present innovations are most easily understood on the basis of our practical examples.

Next, the invention will be clarified further by diagrams and non-limiting examples and figures linked to them.

Example 1

Fabrication of IEChip Devices and Calibration Plots of Tb(III) Label

Silicon Device Fabrication

Devices with oxide covered silicon working electrodes were fabricated from n-type silicon wafers of 0.005-0.018 $\Omega \cdot cm$ resistivity and (111) orientation. The wafers were initially RCA cleaned with SC-1 ($NH_4OH/H_2O_2$ solution at 80 C), dilute HF, then SC-2 ($HCl/H_2O_2$ solution at 80° C.) and wet oxidized at 950° C. for 90 minutes to yield 380 nm field oxide thickness. The oxide was patterned by standard optical lithography and wet etching to define the working electrode areas. Following RCA-cleaning with HF-dip last to remove any native oxide, the thin tunneling oxide of the working electrode was grown by dry oxidation in 10% oxygen at 850 C. Approximately 4 nm of oxide was grown in 20 minutes. Following photolithography, 50 nm of platinum was deposited by sputtering and patterned by lift-off. Electrical contact to the platinum counter electrode is made through contact pads (connected in parallel) on the front of the wafer, while the silicon working electrode is contacted through the wafer backside. Although not always found necessary, the backside contact could be improved by wet etching the wafer backside free of oxide, and sputtering onto it approximately 100 nm of aluminum. FIG. 1 (*a*) presents a schematic cross-sectional view across a WIRE type device (details below).

Glass Device Fabrication

Pyrex glass wafers were initially cleaned with SC-1, and 400 nm of aluminum was sputtered to form the working electrodes, and to serve as a sacrificial layer in the patterning of platinum. First the counter electrode areas were defined by standard optical lithography, and aluminum was removed from those areas by wet etching. The aluminum film was intentionally over etched by 100% to form an overhang structure in the photo resist, which was not removed at this stage. Platinum was then sputtered and patterned by lift-off, facilitated by the overhanging resist. Next the aluminum working electrodes were defined by lithography and wet etching. About 4 nm of aluminum oxide was deposited by ALD from trimethylaluminum and water precursors. This layer was removed from the platinum counter electrode and contact pads by photolithography and etching. Etching was effected by the alkaline photo resist developer solution during two minutes of over development, which the photo resist pattern easily withstands. Finally the photo resist was removed. Electrical contact is made to both the working and counter electrodes through their respective contact pads on the front of the wafer. A schematic cross-section of a glass device is shown in FIG. 1 (*b*).

Electrode Geometry and PDMS Fluidics

Figure 2:
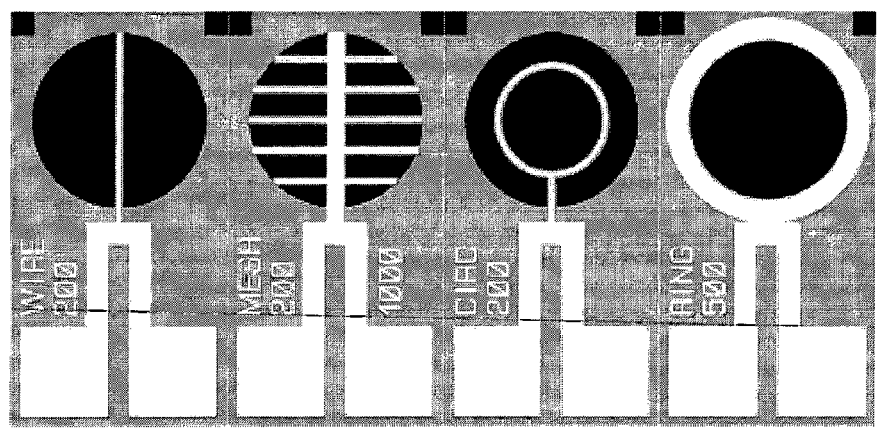
FIG. 2. Some of the electrode geometries tested in silicon devices. Black and white areas represent the working and counter electrodes, respectively. Gray areas are insulation. Indicated on the chip is the electrode type (WIRE, MESH, CIRC, or RING), line width of the counter electrode (200 µm in the first three) and counter electrode line spacing in the MESH devices (1000 µm version is shown).

Several counter electrode geometries were investigated on both glass and silicon devices. FIG. 2 presents some of the silicon designs. Black areas in the figure represent the silicon working electrode covered by the silicon dioxide tunneling dielectric, white areas represent platinum metalization for the counter electrode, while gray areas represent the thick field oxide for electrical insulation. Electrode designs included simple wires running across the working electrode (FIG. 2, WIRE), meshes of wires spread across the working electrode (FIG. 2, MESH), circular counter electrodes within the working electrode area (FIG. 2, CIRC), and ring-shaped counter electrodes fully enclosing the round working electrode (FIG. 2, RING). The line width of the counter electrode was varied, as well as the density of lines in the MESH designs. In all designs, a minimum of 100-µm spacing (insulated by the thick field oxide) was left between the working and counter electrodes. Similar geometries were tested on glass devices.

A master mold for casting PDMS was fabricated on a silicon wafer by processing SU-8 structures on its surface by standard photolithographic techniques. A 50-µm layer of SU-8 50 or a 350-µm layer of SU-8 100 was used for these devices. Multiple layers of SU-8 could be used to create thicker or multilevel structures. Once complete, the master was coated with a 30 nm film of anti-sticking Teflon-like fluoropolymer from a $CHF_3$ plasma in an Oxford PlasmaLab-80+ reactive ion etching system, using 100 sccm flow rate and 50 W RF power. This facilitates easier peeling of the cured PDMS from the master, and prolongs the master's lifetime, without affecting the bonding properties of the PDMS.

The PDMS fluidic chip was fabricated by casting Sylgard 184 silicone elastomer, base and curing agent mixed in a 10:1 ratio, onto the master mold in a Petri dish. The wet PDMS was then out gassed in vacuum and cured at 50 C for 2 hours. The cured PDMS was peeled off the master, cut into individual chips, and bonded to the HECL electrode chips. Bonding was improved by first exposing both the PDMS fluidic chip and the HECL electrode chip to oxygen plasma in a Technics Plasma TePla-400 reactor for 30 seconds, using 800 sccm oxygen flow and 800 W RF power. This plasma treatment also makes the PDMS surface hydrophilic, enabling filling of the sample chamber by capillary force.

Figure 3:
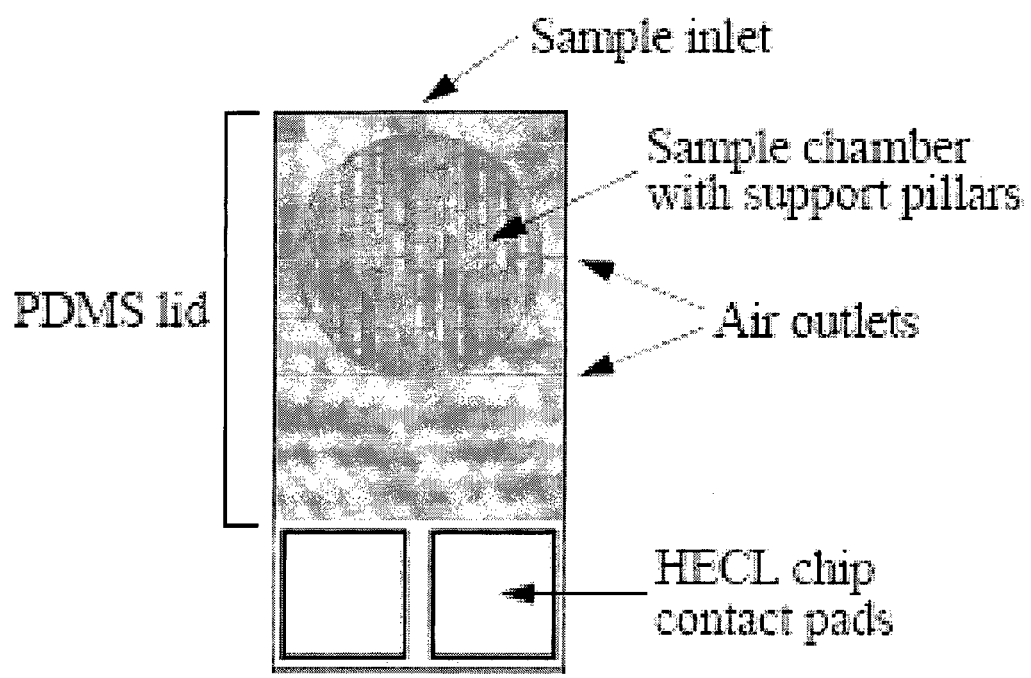
FIG. 3. The PDMS capillary-filling sample chamber.

FIG. 3 shows the geometry of the PDMS lid: An inlet channel at one end of the chip is used to fill the chamber by dipping the chip's edge in sample solution, while multiple channels allow air to escape during filling. Small pillars support the chamber's PDMS ceiling. In the current design, the pillars are evenly distributed throughout the fluidic chamber, not optimized according to the working electrode or counter electrode geometry. The PDMS lid covers only the electrode area of the HECL chip, leaving the electrical contact pads exposed.

Hydrophobic Sample Confinement

Hydrophobic sample confinement on HECL electrode chips was created by depositing a hydrophobic fluoropolymer film in the area around the electrodes. After masking the working and counter electrode areas as well as the electrical contact pads with photo resist, the fluoropolymer film was deposited by the same plasma process as on the SU-8 master in section 2.4, and patterned by lift-off in acetone. The electrodes were thus left uncoated and hydrophilic, whereas the surrounding areas were left strongly hydrophobic.

HECL-Measurements with a Tb(III) Label

Figure 6:
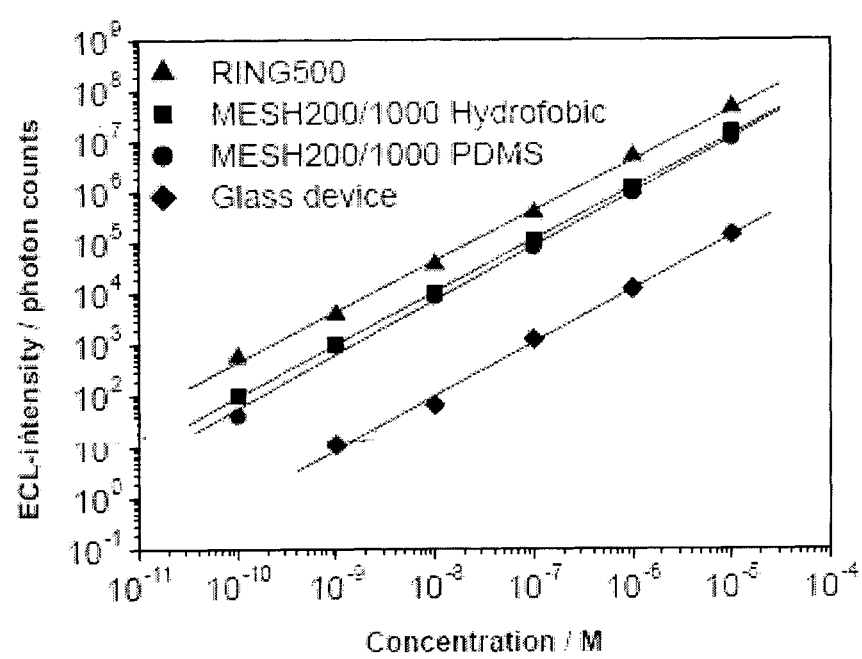
FIG. 6. Calibration curves of Tb(III) chelate using, from top to bottom, a RING 500 device (3-mm solution space above the IEChip), a MESH200/1000 device with hydrophobic sample confinement, a MESH200/1000 device with PDMS fluidics, and a glass device with 3-mm solution space above the IEChip.

A solution of Tb(III) chelated by 2,6-bis[N,N-bis(carboxymethyl)aminomethyl]-4-benzoylphenol was used as the model label. HECL measurements were performed in a sample holder with a photo multiplier tube for optical detection and a 550 nm wavelength 40 nm bandwidth optical interference filter to pass the whole spectral line emitted by the Tb(III) chelate. Front and backside electrical contacts were provided in the sample holder to interface the HECL chip with an in-house built pulse generator. Coulostatic pulses were applied between the on-chip electrodes at a rate of 20 Hz, and luminescence data was measured over a total of 1000 pulses. In order to further improve selectivity, optical detection was performed in a time-resolved manner, integrating luminescence during 6 ms after a 50 µs delay from the end of the pulse. Devices with PDMS fluidics (FIG. 4, left) were filled with the sample solution by dipping the chip's inlet end into a drop of sample solution on the surface of a glass plate. The PDMS chamber filled rapidly by capillary force, and complete filling could easily be verified by eye. The total sample volume was limited by the volume of the PDMS chamber (about 15 µl for the 350 µm high fluidic chambers). Hydrophobically confined samples were pipetted directly onto the electrode chip, until a well-defined, nearly hemispherical drop (FIG. 4, right) was formed within the hydrophobic ring. 100 µl of sample solution was used. The calibration plots of Tb(III) chelate label obtained using several IEChip variants are presented in FIG. 6.

Example 2

Heterogeneous TSH Immunoassays Using Silicon-Based and Glass-Based IEChips

Figure 5:
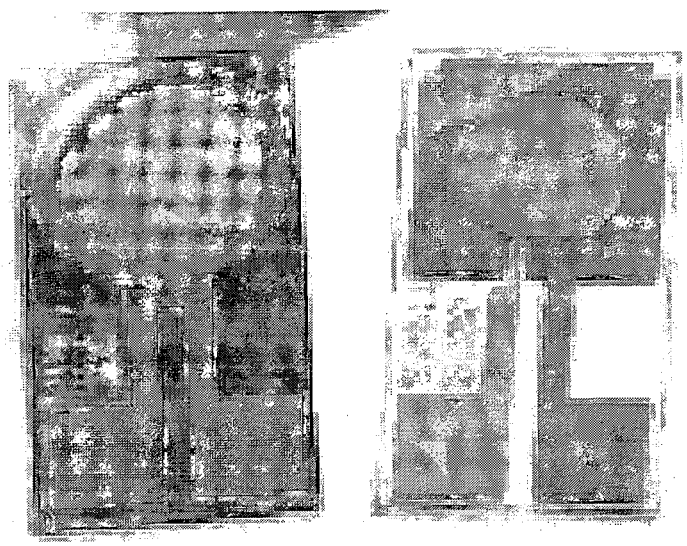
FIG. 5. Silicon and glass-based IEChips with circular working electrode in the middle of the final electrolytic cell.

IEChips used can be seen in FIG. 5, left. The Electrode areas of the IEChips were coated using the aid of the hydrophobic ring on them. The coating solution (150 µL) composed of 0.1 M MES, 0.03 M $H_3BO_3$, 0.5 mM K-citrate, 0.025% glutaraldehyde, 0.05% bovine gamma-globulin and 10 µg/mL of antibody (MIT0406 MOAB anti hTSH Medix Biotech Inc. USA). After incubation for two hours at room temperature in the closed plastic box the coating solution was aspirated and the wells were washed two times with washing solution (50 mM Tris-HCL, pH 7.8, containing 0.9% of NaCl, 0.09% $NaN_3$ and 0.05% Tween 20. The wells were then saturated by adding 300 µl of saturation solution (50 mM Trizma base, 0.1% BSA, 0.1% $NaN_3$, 0.1% Tween 20, pH 7.5 adjusted with $H_2SO_4$). After saturation the IEChips were allowed to dry at 30° C. for 2.5 hours.

Labeled antibody (monoclonal anti-hTSH, clone 5404, 5.5 mg/mL, Medix Biochemica Oy Ab) was prepared by allowing an isothiocyanate derivative of Terbium (III) chelate (Tb-2,6-bis[N,N-bis(carboksymethyl)aminomethyl]-4-bentsoylphenol chelate) to react in 80 times molar excess at pH 9.5 for over night at room temperature. A column 1 cm in diameter filled to 5.5 cm with Sephadex G-50 and for a further 52 cm with Sepharose 6B was used to separate the conjugated protein fraction from excess reagent.

The immunoassay was based on the use of porous film (thickness 6-11 um, $1 \times 10^5 - 6 \times 10^8$ holes/$cm^2$, Whatman). The labeled antibody (0.5 µL, 80 µg/mL) in 50 mM Tris-HCl buffer, pH 7.7, containing 0.05% $NaN_3$, 0.9% NaCl, 0.5% BSA, 0.05% bovine gammaglobulin and 0.01% Tween 20 was pipetted onto the 10×10 mm membrane pieces and they were allowed to dry at room temperature over night.

The standard samples (TSH concentrations 0.1, 1.0, 10.0 and 100.0 mIU/L) were prepared in test tubes by diluting TSH standard solution (Wallac, DELFIA hTSH kit, 324 mIU/mL TSH) with dilution solution (50 mM Trizma base, 0.05% $NaN_3$, 0.9% NaCl, 0.5% BSA, 1 mM $CaCl_2*H_2O$, pH 7.7 adjusted with HCl).

Figure 7:
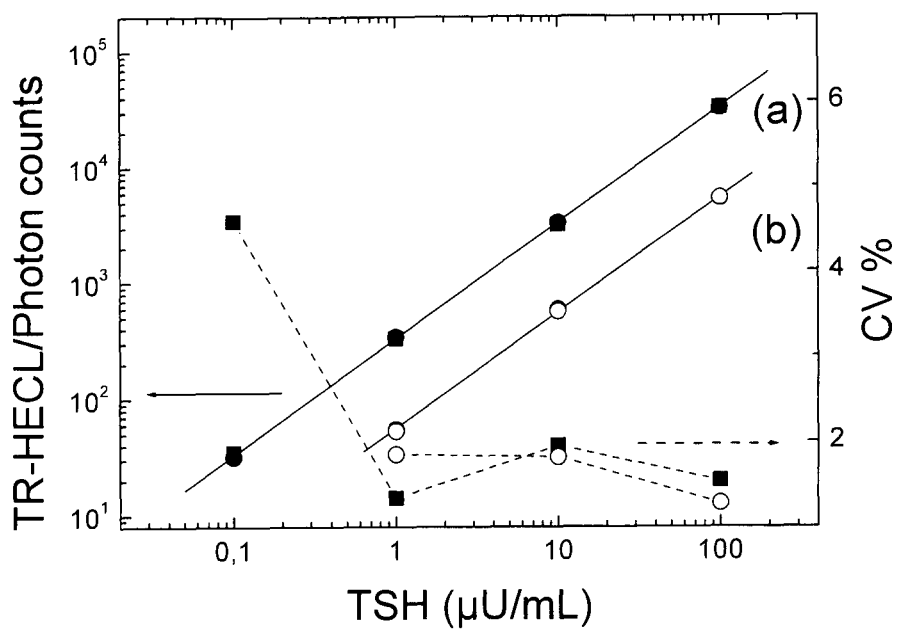
FIG. 7. Heterogeneous TSH immunoassays using silicon-based and glass-based IEChips with hydrofobically surrounded cell areas and using membrane slides in addition of the reagents. (a) Silicon-based IEChips, squares. (b) Glass-based IEChips, circles. Triplicate measurements on each concentration.

For the immunoassay the membrane pieces containing the dried labeled secondary antibody were attached on the hydrophilic electrode area designed to form the electrolytic cell with an electrolytic solution droplet. A 4-µL of sample was pipetted onto the center of porous film on the IEChip. Sample dissolved the labeled antibody and filled fast the cavity between the membrane and electrode network. After 7 minutes the immunoreaction was sufficiently close to the equilibrium, and the membrane was removed by using tweezers. The IEChip was washed 3 times with combined washing/measuring solution (50 mM $Na_2B_4O_7$, 0.1% $NaN_3$, 0.003% Tween 20, pH 7.8 adjusted with $H_2SO_4$). Then, 100 µL of measuring buffer was added and the TR-HECL intensity was measured with an electrochemiluminometer. Measuring instrument was composed of Stanford Research Instruments SR 400 gated photon counter, Nucleus MCS multiscaler card and a home made coulostatic pulse generator and a home made cell compartment (black plastic) and PerkinElmer photon counting CPM module. Pulse amplitude was 25 V, pulse charge 15 µC/pulse, pulse frequency 20 Hz, the TR-HECL intensity was integrated over 200 excitation cycles, delay time 0.05 ms and gate time 6.0 ms. Calibration curve of standard samples is presented in FIG. 7 (a), points marked with squares, triplicate measurements on each concentration. The CV:s were below 2% which has never been seen earlier in any bioaffinity assays carried out by using HECL.

The same procedures were repeated using glass-based IEChips (FIG. 5, right). The results obtained are presented in FIG. 7 (b), points marked with circles, triplicate measurements on each concentration. CV:s were again excellent, clearly below 2%.

Example 3

Figure 4:
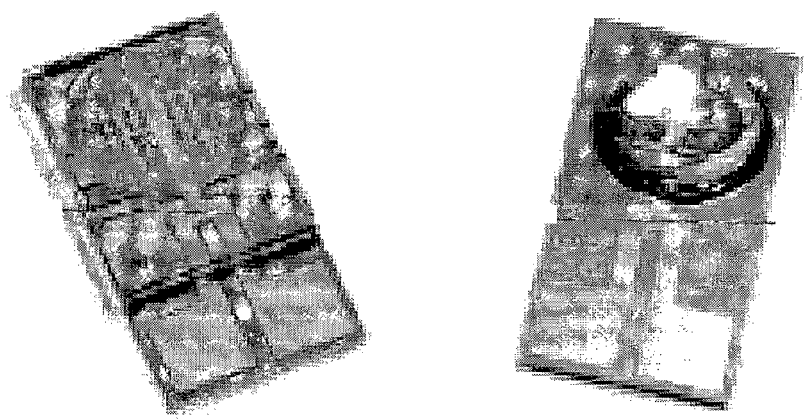
FIG. 4. Silicon-based IEChip with a capillary-filling PDMS chamber (left), and IEChip device with a hydrophobically confined sample droplet (right).

Heterogeneous TSH Immunoassay with Standard Samples Using Silicon-Based IEChips and PDMS Lid The immunoassay was performed in similar way as in Example 2 except silicon-based IEChips of WIRE-type were used (FIG. 4, left). Another exception was that no porous membrane was used and the labeled antibody (0.5 µL, 80 µg/mL) in 0.05 M tetra borate-$H_2SO_4$ buffer (pH 7.7, containing 0.1% $NaN_3$, 0.5% BSA, 0.05% bovine gammaglobulin and 0.01% Tween 20) was pipetted onto the cavity of the PDMS lids and the lids were allowed to dry at room temperature over night.

Figure 8:
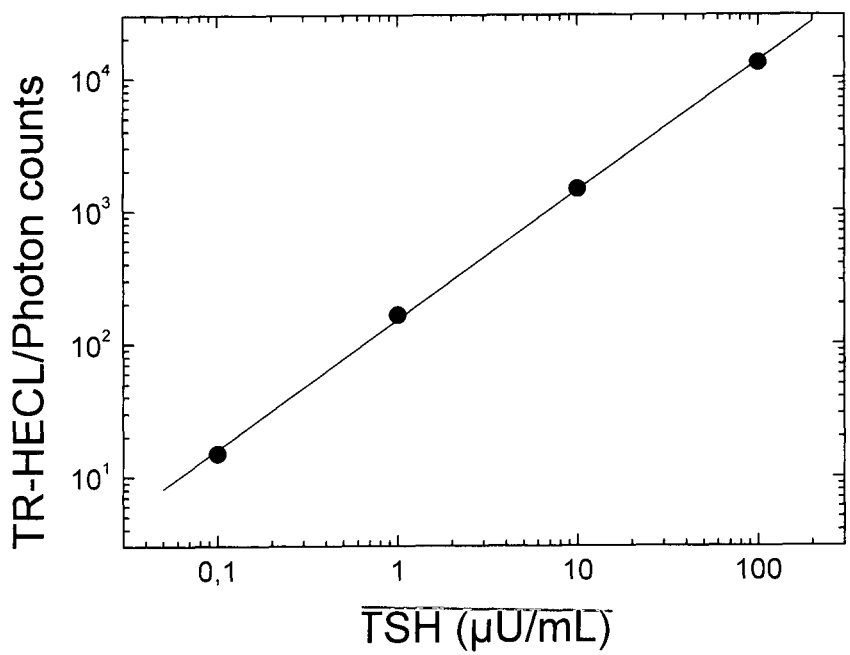
FIG. 8. Heterogeneous TSH immunoassay using silicon-based IEChips and PDMS lid.

Next day the PDMS lids were placed on appropriate position and they were clamped to be tightly against each IEChip. Then the sample diluted in 150 µL of buffer (0.05 M tetraborate-$H_2SO_4$ buffer, pH 7.7, containing 0.1% $NaN_3$, 0.5% BSA, 0.05% bovine gammaglobulin and 0.01% Tween 20) and pipetted in the inlet of PDMS-IECP cartridge prototype. It seemed that the cavity could have been equally well filled also by capillary forces alone. The TR-HECL intensities were measured after exactly 20.0 min incubation time (pulse amplitude was 25 V, pulse charge 15 µC/pulse, pulse frequency 20 Hz, the TR-HECL intensity was integrated over 200 excitation cycles, delay time 0.05 ms and gate time 6.0 ms.). Calibration curve of standard samples is presented in FIG. 8.

Example 4

Probing Assay of Viral RNA on Silicon-Based IEChip

The similar IECHips as in the Example 3 were used but this time with hydrophobically confined miniature "cell". First, A 120-nt PCR fragment was amplified using viral RNA as target (Lönnrot et al., J. Med. Vir. 56 (1999) 378-84.) This region is diagnostic target in centralized diagnostic laboratories for routine analysis of entero- and rhinoviruses, which are important respiratory and CNS pathogens.

Catching probe (C-probe,TTA-GCC-GCA-TTC-AGG-GGG-CGA-AAA-AA-C6-NH2 (SEQ ID NO:1), MedProbe As) complementary to the template strand of the 5'-end of picorna-RNA was immobilized to oxide-coated silicon electrodes (IEChip, FIG. 2, Example 3). The C-probe was designed to have poly A-tail followed by specific primer to which denatured PCR product was allowed to anneal. The catching probe was bound to silanized (APTES) silicon oxide surface of THE IEChip by the six carbon aliphatic carbon and end amino group via DSS-reagent (disuccinimidyl suberate) according to manufactures instructions.

The detection probe (NH2)4-GA-AAC-ACG-GAC-ACC-CAA-AGT-A) (SEQ ID NO:2)) was labelled with the isothiocyanate derivative of Terbium-chelate (Tb-2,6-bis[N,N-bis (carboxymethy) aminomethyl]-4-benzoylphenol chelate) by incubating the probe with 80 times higher molar excess of the chelate in 0.5 molar sodium carbonate buffer (pH9.5). After over night incubation the labeled probe was purified by Sephadex G50 column (NAP-5 column, GE Healthcare)

Figure 9:
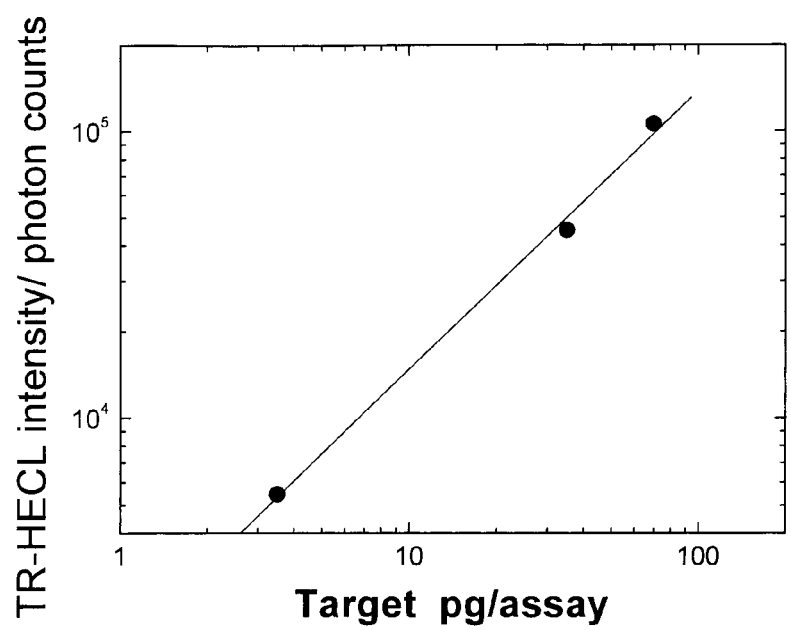
FIG. 9. Probing assay of viral RNA on silicon-based IEChips.

Hybridization assay of human entero- and rhinoviruses was done as follows. After RT-PCR amplification, the DNA sample (PCR amplified sample diluted 1:50, 1:100 and 1:1000, 20 µL) was denatured by adding 180 µl of 50 mmol/L NaOH (5 min at 37° C.) and the neutralized by adding 200 µL of neutralization buffer (6×SSC, 0.3% Tween 20, mmol/L citric acid). Thereafter 10 µL of this neutralized sample and 10 µL of Tb-labeled probe (0.6 ng/µL, 50 mmol/L Tris-HCl buffer, pH 7.8, 600 mmol/L NaCl, 1% Triton X 100 and 1% Blocking reagent (Roche) were taken into a new tube and after mixing finally 5 µL of this solution was taken onto the membrane on the IEChip. Within 8 minutes at ambient temperature the reaction is sufficiently close to the equilibrium and after removing the membrane from the IEChip, the IEChip was washed 3 times and the TR-CECL measured. The sample dilution curve is presented in FIG. 9.

Example 5

EE-Solutions for Different Type of the Cartridges

Each cartridge type need a specific solution of the applied IEChip, which takes into the consideration of the electrolyte solution layer thickness and electrolyte and buffer solution composition needed in the assays. We are confident that in any type of cartridges wherein the present electrode area is appropriate the right solution based on silicon chips can be chosen from example designs from FIG. 10 (a) and glass and other insulating substrate-based chips from FIG. 10 (b).

Figure 10:
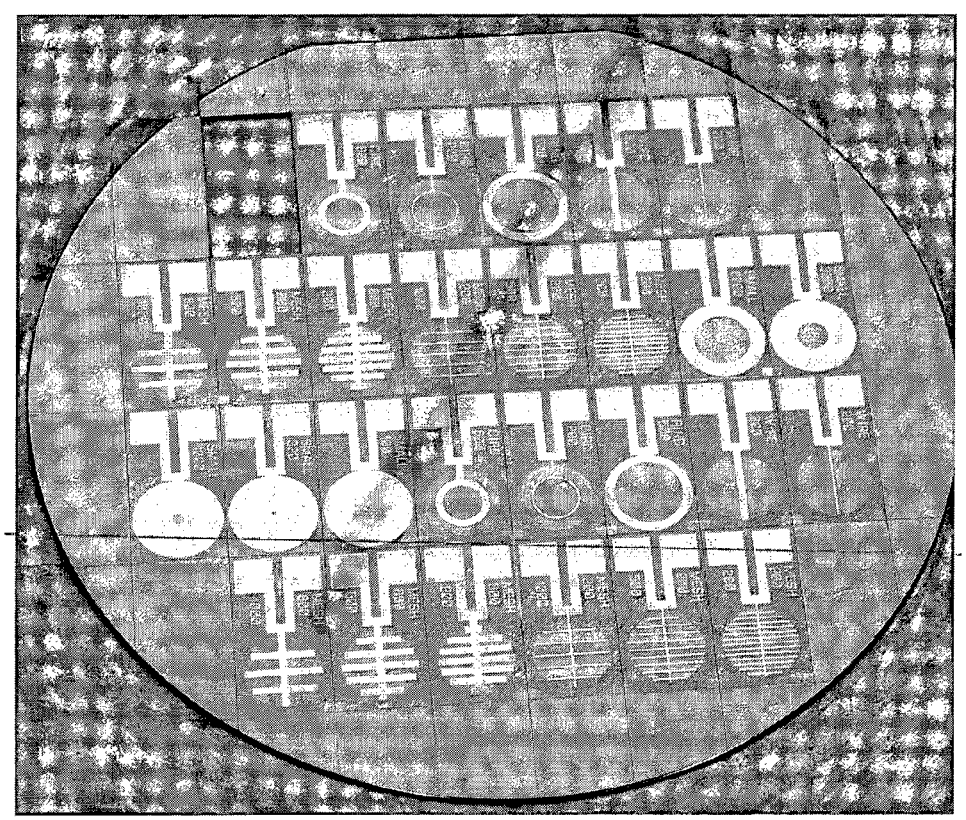
FIG. 10. IEChip solutions for different type of the cartridges. Specific IEChip solutions for different type of cartridges made of silicon (a) and made on glass (b).
Figure 10:
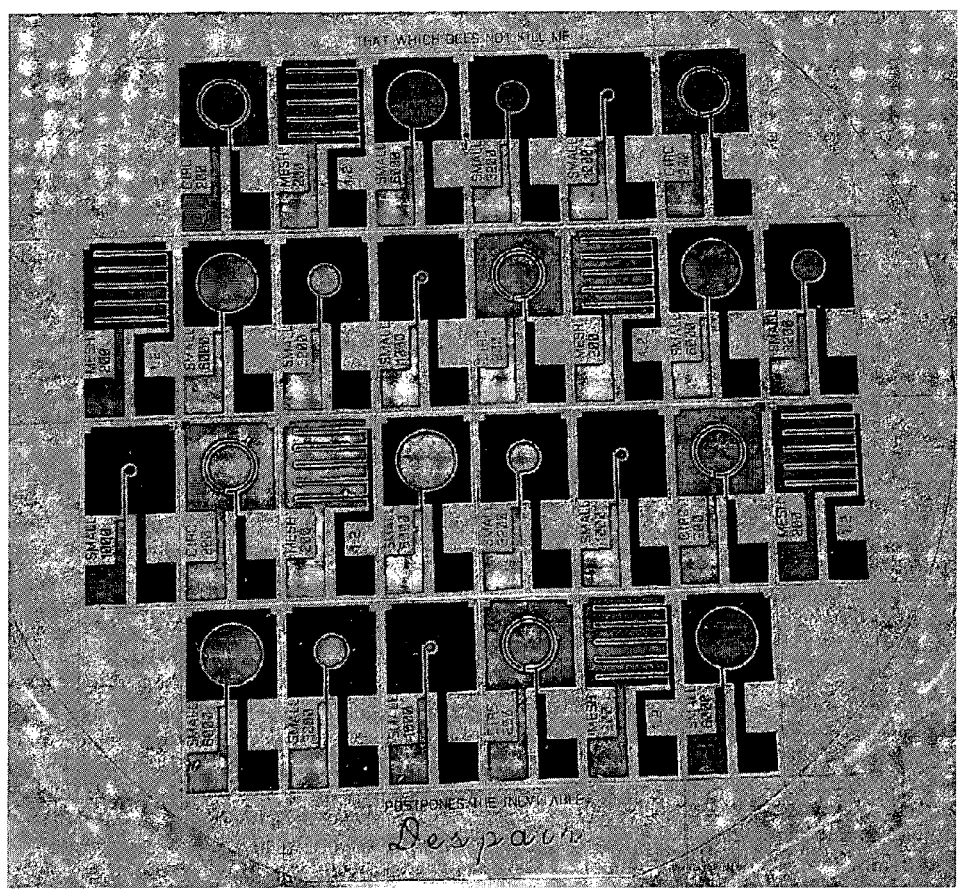

In FIG. 10 (a), the mirror-looking areas are made of metal films such as from platinum usable as counter electrodes, and the gray areas are the working electrode areas coated with an ultra thin ca. 4-nm silica film. The green areas are coated with a thick insulating film/films.

In FIG. 10 (b), the (blue) plastic film shown is needed to protect the chips during the slicing, but is easily removable from the final chips. The transparent areas are just glass and the lighter non-transparent areas are working electrode areas and darker areas counter electrode areas, respectively. Take also a closer look at one type of these IEChips in FIG. 5, right.

The invention claimed is:

1. An analytical system to determine an amount of an analyte said system comprising a disposable hot electron-induced (HECL) electrochemiluminescent analytical cartridge and a luminescence measurement instrument comprising excitation electronics said cartridge comprising:
   a HECL electrode chip;
   and
   a lid bonded to the electrode chip;
   wherein the chip comprises a working electrode and a counter electrode integrated on a same plane of the chip and electrode contact pads connected to the working electrode and the counter electrode through which the working electrode and the counter electrode can be connected to the excitation electronics of the luminescence measurement instrument;
   the lid covering only the working electrode and the counter electrode of the chip leaving the electrode contact pads of the chip exposed;
      the lid having an inlet channel at one end of the chip, said channel leading to a sample chamber formed between the lid and the electrode chip, and said channel allowing filling of the sample chamber with a sample by capillary force;
      the working electrode being a conductor or strongly doped semiconductor, said conductor or semiconductor being covered by an electrical insulator layer, and said working electrode serving as a cathode;
      the counter electrode being made of metal by sputtering or vacuum evaporation and said counter electrode serving as an anode;
   said chip being made of an insulating material or partially of a conducting and partially of an insulating material in a way that the conducting material provides an electronic contact either to the anode or to the cathode and the insulating material prevents a galvanic contact between the electrodes;
   wherein the chip will produce luminescence signals recorded by the luminescence measuring instrument when electrical pulses are fed in the chip, and
   wherein the luminescence signals produced during or after the pulses are proportional to the amount of an analyte.

2. The system according to claim 1, wherein the counter electrode has a shape selected from the group consisting of wire- or mesh-shape across the working electrode, and ring- or circular-shape around the working electrode, and wherein a minimum of 100 μm spacing insulated a by field oxide is left between the working and counter electrodes.

3. The system according to claim 1 wherein:
   the sample chamber has hydrophilic surface, thereby improving filling the chamber with a sample by capillary force.

4. The system according to claim 1, wherein the sample chamber formed between the lid and surface of the electrode has a thickness of about 3.0 mm;
   and wherein while the sample or diluted sample is filling the sample chamber it dissolves all the necessary reagents from the entrance inlet,
   for the bioaffinity- and electrochemical reactions to take place in the sample chamber.

5. The system according to claim 4, wherein the chamber is capable of being washed once with a measuring buffer prior to excitation.

6. A method for a bioaffinity assay comprising the steps of:
   a) bringing an analytical sample into the sample chamber of the system of claim 1;
   b) allowing the sample to react with reagents,
   c) exciting the sample by electrical pulses to generate luminescence; and
   d) measuring the luminescence.

7. The method of claim 6, wherein the bioaffinity assay is a nucleic acid probing assay or immunoassay.

* * * * *